US00PP15807P3

(12) United States Plant Patent
Chahbandar

(10) Patent No.: US PP15,807 P3
(45) Date of Patent: Jun. 28, 2005

(54) ARTICHOKE PLANT NAMED 'BCL 9-11'

(50) Latin Name: *Cynara scolymus L.*
Varietal Denomination: Globe

(76) Inventor: Medhat Chahbandar, Domaine La Quintane, Torrielles (FR), 66440

( * ) Notice: Subject to any disclaimer, the term of this patent is extended or adjusted under 35 U.S.C. 154(b) by 0 days.

(21) Appl. No.: 10/371,511

(22) Filed: Feb. 20, 2003

(65) Prior Publication Data

US 2004/0168239 P1 Aug. 26, 2004

(51) Int. Cl.[7] ..... A01H 5/00
(52) U.S. Cl. ..... Plt./258

(58) Field of Search ..... Plt./258

(56) References Cited

U.S. PATENT DOCUMENTS

PP12,206 P2 11/2001 Cofer
PP12,208 P2 11/2001 Cofer

*Primary Examiner*—Anne Marie Grunberg
*Assistant Examiner*—Annette H Para
(74) *Attorney, Agent, or Firm*—Kenneth A. Weber

(57) ABSTRACT

A new and distinct cultivar of Artichoke plant named 'BCL 9-11' characterized by numerous very large semi-glossy heads and thick, fleshy bracts and hears. The heads is rounder than the parent lines with reduced pubescence. The bracts are more compact that its parents.

3 Drawing Sheets

BACKGROUND OF THE INVENTION

The present invention comprises a new and distinct cultivar of artichoke plant, botanically known as *Cynara scolymus L.,* and herein referred to by the cultivar name 'BCL 9-11'. This new variety is characterized by exhibiting very large semi-glossy fruit heads that have weighed more than 900 gm., and thick, fleshy bracts and hears. The fruit heads are rounder than the parent lines with reduced pubescence. The bracts are more compact that its parents.

*Cynara scolymus L.,* commonly known as 'Globe' artichoke, is a perennial herb and is a member of the family Asteraceae, also known as the Compositae family. 'Globe' artichokes comprise: leaves, which are pinnately lobed, but primarily spineless; globose capitula composed of overlapping layers of large involucral bracts; and receptacles, which are enlarged and fleshy. Globe artichoke plants are essentially grown for the production of the immature flower heads (or buds). The immature buds are harvested before the appearance of sexual organs (or the mature flower) and are considered vegetable delicacies. Fresh artichokes may be steamed, boiled, or baked after which the fleshy receptacle, inner and outer bracts, and parts of the floral stem may be eaten.

The new cultivar is a product of a planned breeding program carried out by the inventor, M. Chanbandar near Perpignan, France. It was selected from a hybrid crossing of the artichoke variety 'BH 35-22' (unpatented) and the artichoke variety 'BCA 3-21' (U.S. Plant patent application Ser. No. 10/372,050). The inventor performed asexual reproduction of the new cultivar via division near Perpignan, France. It was demonstrated that the combination of characteristics as herein disclosed for the new cultivar are firmly fixed and retained through successive generations of sexual reproduction.

BRIEF DESCRIPTION OF THE INVENTION

The following traits have been repeatedly observed and are determined to be basic characteristics of 'BCL 9-11'.

These traits in combination distinguish the artichoke as a new and distinct cultivar from the parent and any other variety known to the breeder. The parent varieties listed above are, to the inventors knowledge, the closest prior art to the claimed plant variety. 'BCL 9-11' has very large semi-glossy fruit heads (that have weighed more than 900 gm.), and exhibits thick, fleshy bracts and hears. The heads is rounder than the parent lines with reduced pubescence. The bracts are more compact that its parents.

'BCL 9-11' has not been observed under all possible environmental conditions. The phenotype of the new cultivar may vary with variations in environment such as temperature, humidity, light intensity and day length, without any change in the genotype. However, the following observations, measurements and values, describe the new cultivar as grown in Lompoc, Calif. under conditions which closely approximate those generally used in horticultural practice.

Lompoc is located on California's central cost in Santa Barbara County. Conditions can vary in the summer months. Air temperatures can range between the low 60's to 80's. The relative humidity is generally high. Prevailing winds are northwesterly and rainfall averages 12 inches per year.

In the following description, holding quality was measured by the physical appearance of the head. This includes the head's appearance following 3 and 7 day storage periods in cold storage at 34° F. The head's exterior (oxidation) was observed at each of the two observation points. Browning and blackening of plant tissue was evaluated as light, moderate and extreme. Overall storage response was measured by observing heads following 3 and 7 day cold storage periods. These observations concentrated on visible color variability and/or presence of lesions or other cosmetic anomalies. Leaf ratio (L/W) was determined by dividing representative leaf sample lengths by their width. Finally, head response (weather) was determined by observing the heads at maturity. These field observations focus on the presence or absence of bronzing, necrotic or chlorotic lesions or any abiotic responses to environmental conditions.

BRIEF DESCRIPTION OF THE DRAWINGS

This new variety is illustrated by the accompanying photographic drawings, with such colors in the photograph being as true to those of the plant as can be reasonably obtained from conventional photographic procedures. In such photographs.

DETAILED DESCRIPTION OF THE INVENTION

Figure 1:
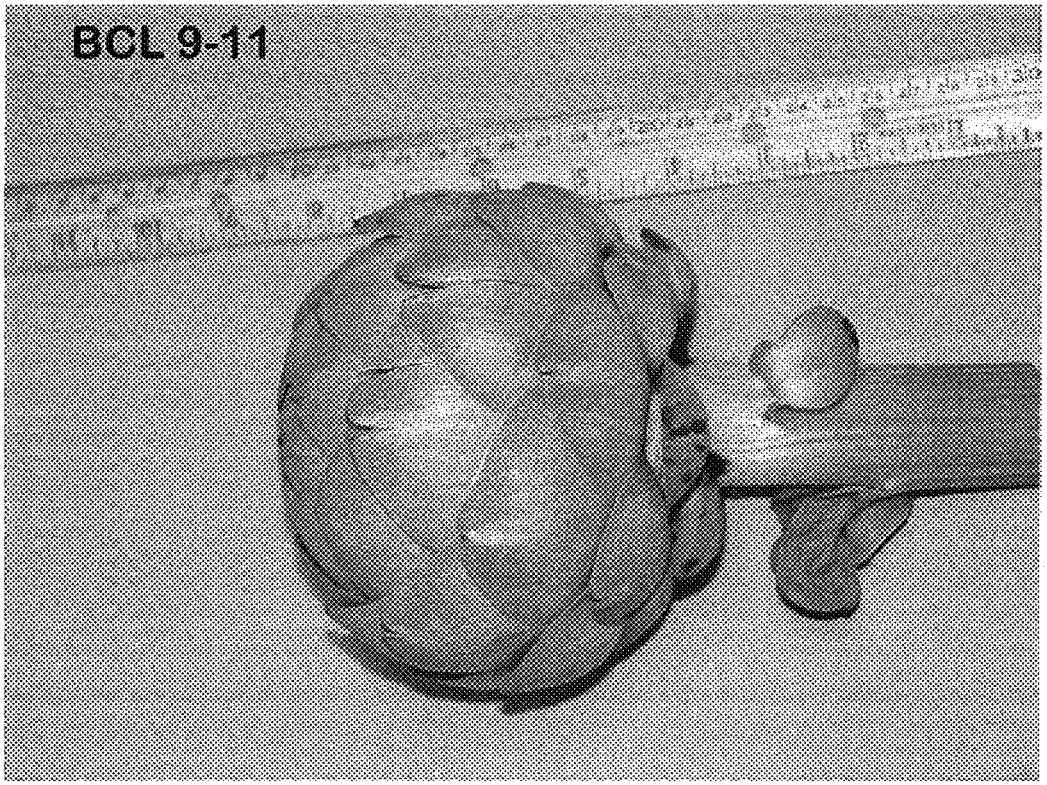
FIG. 1 shows a side elevational view of 'BCL 9-11's fruit in full color.
Figure 2:
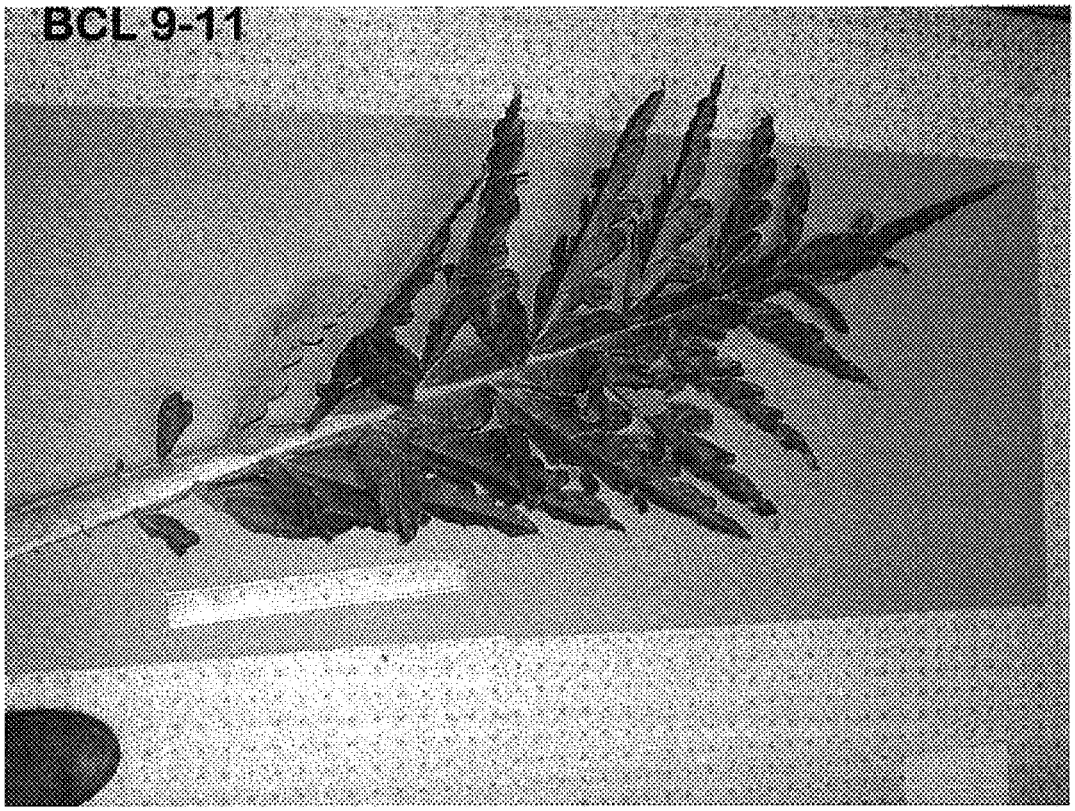
FIG. 2 shows a side elevational view of 'BCL 9-11's foliage in full color.
Figure 3:
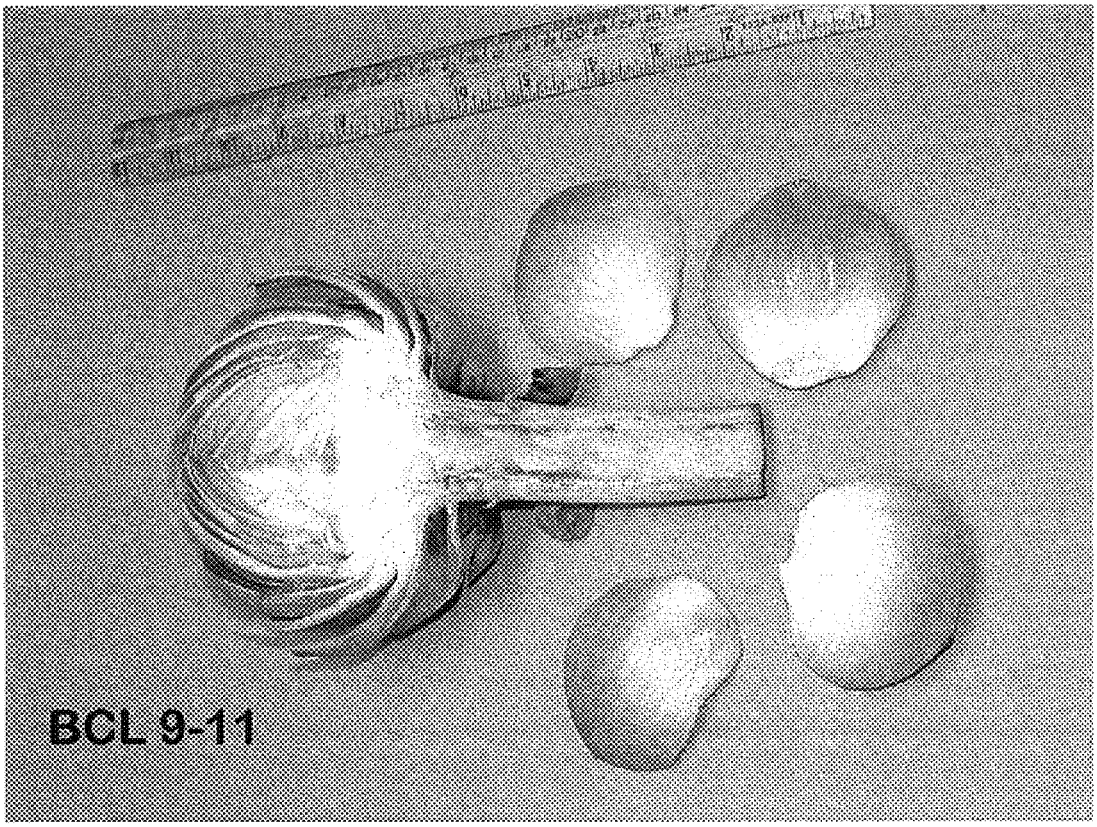
FIG. 3 shows a close-up view of the vertical cross-section of 'BCL 9-11's fruit in full color.

The following observations, measurements, and values describe the new artichoke plant is based upon observations of plants grown in Lompoc, Calif. The data was collected from tissue culture plants grown in Perpignan and acclimatized in California. Selections were made in outdoor field settings. The plants were grown in the soil in rows where row spacing (bed centers) was at 80 inches, and individual plant spacing at 24 inches. The plants were than planted in July and the observations described therein taken in December of the next year. Color references are measured against The Royal Horticultural Society Colour Chart.

General:

*Parentage.*—Hybrid cross with 'BH 35-22' and 'BCA 3-21'.

*Classification.*—*Cynara Scolymus* L. cv 'BCL 9-11'.

*Propagation.*—Asexual propagation by division.

Plant:

*Height.*—119.4–139.7; average 127.0 cm.

*Width.*—213.4–243.8; average 221.5 cm.

*Form.*—Full.

*Growth habit.*—Upright.

*Vigor.*—Vigorous.

Side shoots:

*Number.*—1–5 shoots per plant; average 2.6 shoots per plant.

*Length.*—22–44 cm; mean 32 cm.

*Diameter.*—2–3 cm; mean 2.4 cm.

*No. of leaves per shoot.*—2–4 leaves.

*Development.*—Vigorous.

*Color.*—Green group 143 b.

*Foliage density.*—Dense.

Capitulum:

*Size* (*primary*).—Approximately 14 cm.

*Shape.*—Round compact with a flat top.

*Texture.*—Hard and smooth.

*Fragrance.*—Mild.

Bract:

*Length.*—Approximately 7 cm.

*Width.*—Approximately 5 cm.

*Shape.*—Ovate bract, medium to short length of base, medium to broad width of base, thick, slightly longer than broad.

*Texture.*—Hard and smooth.

*Number per plant.*—202.

*Color* (*inner*).—Green group 147 c–d.

*Color* (*outer*).—Green group 147 c.

*Firmness.*—Firm and fleshy with thick basal thickness.

*Spinosity.*—None, or minimal — less than 1 mm.

*Basal thickness.*—6–17 mm.

Miscellaneous:

*Heart description.*—Concave full, well developed, with flat shoulders resembling a "v" with thick bract connection, broader than 'Green Globe'.

*Receptacle thickness.*—1.7 cm.

*Heart color.*—Yellow green group 145 c–d.

*Florets.*—Sterile.

*Pappus length.*—1.2 cm.

*Pappus color.*—Yellow green group 145 d.

*Head firmness.*—Firm, heads are dense and solid.

*Gloss.*—Less glossy than 'Green Globe'.

*Cold storage response.*—Slight leaf discoloration with a medium brown cut stem. Stem was semi-soft after 7 days.

*Head response* (*weather*).—After freeze the outer bracts would blister, but not discolor.

Foliage:

*Shape.*—Long strap-like leaves with irregular dentate.

*Main stem diameter.*—7.0–11.4; cm average 8.7 cm.

*Main stem length.*—Approximately 120.7–156.2 cm.

*Main stem width* (*w/leaves*).—Approximately 50.8–83.8 cm.

*Distance between main lobes.*—Approximately 8.4–11.5 cm.

*No. of leaves on main stem.*—15–18 leaves.

*Leaf ratio.*—Approximately 1.9–2.4 cm.

*Leaf area.*—Approximately 2,412–5,155 cm sq.

*Upper leaf surface color.*—Green Group 137a–b.

*Lower leaf surface color.*—Green group 137c–d.

*Texture.*—Slightly but uniformly textured.

*Pubescence.*—Sparse, some visible pubescence on lower leaf surface.

*Lobe width.*—Approximately 8.9–15.2 cm.

*Lobe indentation.*—Approximately 4.5–8.8 cm.

*Petiole length.*—Approximately 12.2 cm.

*Petiole width.*—4.92 cm.

*Petiole thickness.*—Approximately 1.9 cm.

*Petiole color.*—Green group 141 c.

Seeds: None observed.

What is claimed is:

1. The new distinct variety of artichoke plant substantially as shown and described, characterized particularly as to novelty by the characteristics listed above.

* * * * *